United States Patent [19]

Lauks

[11] Patent Number: 4,551,209
[45] Date of Patent: Nov. 5, 1985

[54] METHOD OF CALIBRATING CONDUCTIVE METAL OXIDE ELECTRODES

[75] Inventor: Imants R. Lauks, Sewell, N.J.

[73] Assignee: Integrated Ionics, Inc., Princeton, N.J.

[21] Appl. No.: 572,200

[22] Filed: Jan. 19, 1984

[51] Int. Cl.⁴ ............................................. G01N 27/00
[52] U.S. Cl. .................................... 204/1 T; 204/401; 73/1 G
[58] Field of Search ................. 204/1 T, 401; 73/1 G, 73/1 R; 204/402

[56] References Cited

U.S. PATENT DOCUMENTS

| | | | |
|---|---|---|---|
| 3,556,950 | 1/1971 | Dahms | 204/1 T |
| 3,681,255 | 8/1972 | Wilfore | 204/1 T X |
| 3,698,238 | 10/1972 | Wall et al. | 73/1 R |
| 3,824,157 | 7/1974 | Macur | 128/635 X |
| 4,109,505 | 8/1979 | Clark et al. | 73/1 R |

Primary Examiner—Andrew H. Metz
Assistant Examiner—Nam X. Nguyen
Attorney, Agent, or Firm—Pennie & Edmonds

[57] ABSTRACT

A conductive metal oxide electrode can be calibrated by immersing the electrode and a reference electrode in a solution of known pH and applying to them a setting potential which is approximately equal to the steady state potential that would be observed for that electrode with respect to the reference electrode in a solution of that value of pH.

2 Claims, 2 Drawing Figures

METHOD OF CALIBRATING CONDUCTIVE METAL OXIDE ELECTRODES

Related applications are "Ambient Sensing Extended Gate Transistor," Ser. No. 572,182; "Ambient Sensing Devices," Ser. No. 572,199; "Integrated Ambient Sensing Devices and Methods of Manufacture," Ser. No. 572,185, and "Ambient Sensing Devices Using Polyimide," Ser. No. 572,213, filed concurrently herewith, and "Amphorous Metal Oxide Electrodes," Ser. No. 441,902, filed Nov. 15, 1982, which are incorporated herein by reference.

BACKGROUND OF THE INVENTION

This relates to a method of calibrating conductive metal oxide electrodes and in particular to a method of setting the offset potential for such electrodes.

One problem which exists with all ion selective electrodes is that each electrode must be calibrated individually by determining an offset potential $E_0$. For electrodes made of a combination of a metal and a thin metal oxide such as antimony/antimony oxide ($Sb/Sb_2O_3$), palladium/palladium oxide ($Pd/PdO$) and iridium/iridium oxide ($Ir/IrO_2$), the potential determining reaction involves protons such that the equilibrium equation between the metal and metal oxide has a form such as

$$IrO_2 + 4H^+ + 4e \rightleftharpoons Ir + 2H_2O. \qquad (1)$$

With respect to metal oxide electrodes wherein the metal is selected from the platinum or rhenium groups of metals such as those disclosed in application Ser. No. 441,902, the potential determining reaction involves two valence states of the hydrated oxide such that the equilibrium equation, for example, for thick iridium oxide has the form

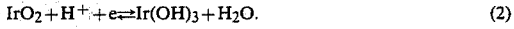

$$IrO_2 + H^+ + e \rightleftharpoons Ir(OH)_3 + H_2O. \qquad (2)$$

Because this chemical reaction is independent of the material on which the oxide is deposited, thick metal oxide electrodes can be coated onto metals other than the metal of the metal oxide or onto insulators as disclosed in application Ser. No. 441,902.

In the case of thick iridium oxide electrodes, the open circuit cell potential is specified by the equation $$E = E_0 + (kT/q) \log_{10} [H^+] \qquad (3)$$

where the offset voltage $E_O$ depends on the relative amounts of the hydrated iridium oxides of the two valence states. Thus, the output potential from a thick metal oxide of the platinum or rhenium groups depends on the concentration of hydrogen ions as is required in order to use such an electrode to sense pH. As will be apparent, the output potential also depends on the value of $E_0$ which is the offset potential. In order to calibrate the electrode this value must be determined independently for each electrode, a time-consuming process.

In addition, the offset voltage $E_O$ is a time-dependent quantity when the electrode is kept in an open circuit, being dependent on the extent of hydration of the iridium oxide at the time of the offset voltage measurement. For example, if an open circuit electrode is immersed in an aqueous solution, $E_0$ will move gradually with time, settling to a steady state potential of approximately 600 milliVolts vs. the potential of a saturated calomel reference electrode as shown in the data of FIG. 1. Such data is reproduced from T. Katsube et al. "pH Sensitive Sputtered Iridium Oxide Films," *Sensors and Actuators*, vol. 2, p. 399 (1982) which is incorporated herein by reference.

SUMMARY OF THE INVENTION

I have found that an electrode comprising a thick metal oxide which is an electrical conductor can be calibrated by immersing the electrode in a solution of known pH and applying to it a closed circuit setting potential which is approximately equal to the steady state potential that would be observed on that electrode in a solution of that value of pH if it had been allowed to stabilize slowly in open circuit conditions as in the case of FIG. 1. In practicing the invention, it was sufficient to subject the electrode to this potential for approximately 30 minutes. Moreover, the invention can be used and has been used to calibrate more than one electrode at the same time.

BRIEF DESCRIPTION OF THE DRAWINGS

These and other objects, features and advantages of the invention will be more readily apparent from the following detailed description of a preferred embodiment of the invention, which is provided by way of illustration, in which.

DESCRIPTION OF PREFERRED EMBODIMENT

Figure 2:
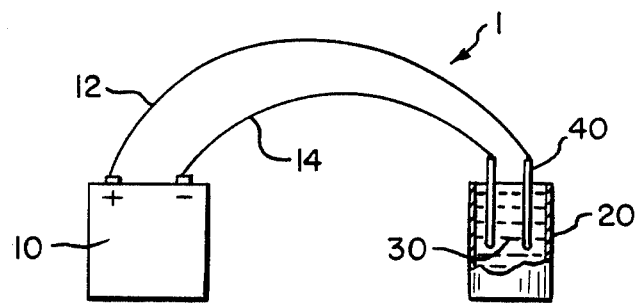
FIG. 2 is an illustration of illustrative apparatus for calibrating an amorphous metal oxide electrode.

As shown in FIG. 2, apparatus for calibrating a metal oxide electrode comprises a DC power supply 10, a tank 20 in which there is an aqueous solution 30 of known pH, and wires 12, 14 for applying a potential to electrodes that are immersed in the tank. As shown, one lead 12 is connected to an electrode 40 that is to be calibrated and the other lead 14 is connected to a reference electrode 50. Illustratively, the reference electrode is a saturated calomel reference electrode.

Figure 1:
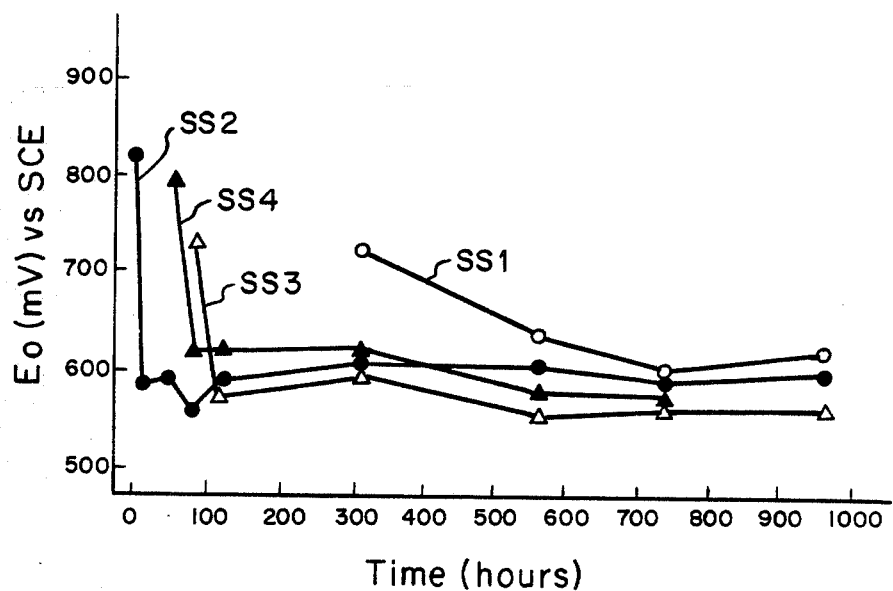
FIG. 1 is a graph depicting the change with time in the value of the offset voltage with respect to the potential of a saturated calomel reference electrode on an amorphous iridium oxide electrode in an open circuit in a solution of known pH.

As indicated by equation (3), the potential that is observed on a metal oxide electrode varies with the concentration of hydrogen ions in the solution. This potential decreases with increasing value of pH at a rate of approximately 60 milliVolts/pH at room temperature. To calibrate the electrode, a voltage is applied to the electrode that has a value approximately the same as the steady state voltage that would be observed on that electrode when immersed in a solution of the same pH if it were allowed to achieve stability under open circuit conditions as shown in FIG. 1. This close-circuit voltage is applied for a long enough time so that the value of the offset voltage, $E_0$, does not substantially drift from said steady state voltage when the electrode is subsequently used as a sensor in open circuit conditions to sense the ambient chemical activity of ionic species. In practice, approximately 30 minutes has been sufficient to effect this change. The voltage is then disconnected and the electrodes removed from the solution. At this point, each of the electrodes will be found to have approximately the same open circuit potential and the electrodes will maintain approximately this potential over periods of time such as one week. If after an appreciable lapse of time it is found that the calibration may have drifted, the electrode may be recalibrated simply by repeating the process.

EXAMPLE

In practicing the invention, four iridium oxide electrodes were prepared by sputter-coating the iridium oxide onto 5 mm×0.5 mm diameter nylon rods. An electrical contact was made to the iridium oxide at one end of the rod and the iridium oxide at the other end was left exposed. The exposed ends of the four electrodes were then dipped in a pH 4 buffered solution at 20° C. together with a saturated calomel reference electrode. The four electrodes were then connected to one terminal of power supply 10 and the calomel reference electrode to the other terminal. The power supply was set to establish a 290 mV potential difference between the four electrodes and the calomel reference electrode, 290 mV being the approximate steady state potential on an iridium oxide electrode referenced to a saturated calomel reference electrode in a solution having a pH of 4. After 30 minutes the electrodes were disconnected and removed from the solution. The open circuit pH response of the electrodes was measured over a period of one week. All electrodes had the same open circuit potential at pH 4 which was 290.0±0.1 mV. All the electrodes had theoretical slopes of 2.303 kT/q. One electrode which was monitored carefully over several days was shown to be stable to 1 mV during that period and had short term stability (one hour) as good as 0.1 mV.

Because they all have similar equilibrium equations, this method may be used for any conductive metal oxide electrode wherein the metal oxide is an oxide of the metals selected from the group of platinum and rhenium group metals.

While the invention has been described in conjunction with a specific embodiment, it is evident that numerous alternatives, modifications, and variations will be apparent to those skilled in the art in light of the foregoing description.

What is claimed is:

1. A method for calibrating conductive metal oxide electrodes wherein the oxide is an oxide of a metal selected from the group consisting of platinum and rhenium group metals comprising the steps of:
   immersing said metal oxide electrode into a solution of known pH;
   immersing a reference electrode into said solution, and
   applying across said metal oxide electrode and said reference electrode a potential equal to approximately the steady state potential that is observed for a second electrode having substantially the same chemical composition as said metal oxide electrode when said second second electrode is immersed in a solution of the same pH and is allowed to stabliize slowly in open circuit conditions.

2. The method of claim 1 wherein said metal oxide electrode is an iridium oxide electrode.

* * * * *